(12) United States Patent
Kornel

(10) Patent No.: US 8,152,792 B1
(45) Date of Patent: Apr. 10, 2012

(54) SUBCUTANEOUS DRAIN FOR A BODY CAVITY

(76) Inventor: Ezriel E. Kornel, Bedford Hills, NY (US)

(*) Notice: Subject to any disclaimer, the term of this patent is extended or adjusted under 35 U.S.C. 154(b) by 815 days.

(21) Appl. No.: 12/206,161

(22) Filed: Sep. 8, 2008

(51) Int. Cl.
  *A61M 1/00* (2006.01)
  *A61M 27/00* (2006.01)
  *A61N 1/30* (2006.01)

(52) U.S. Cl. ............ 604/540; 604/19; 604/21; 604/317; 604/541

(58) Field of Classification Search .................. 604/540, 604/236, 905, 19, 4, 8–10, 174–175; 220/137, 220/232, 4.06, 657; 128/912; 600/205, 201; 606/108; 607/19, 45, 180
See application file for complete search history.

(56) References Cited

U.S. PATENT DOCUMENTS

| | | | | |
|---|---|---|---|---|
| 3,310,051 A * | 3/1967 | Schulte | .......................... | 604/175 |
| 4,081,789 A * | 3/1978 | Markwitz | ..................... | 714/789 |
| 4,673,394 A * | 6/1987 | Fenton et al. | ................. | 604/175 |
| 4,677,985 A | 7/1987 | Bro et al. | | |
| 5,041,098 A * | 8/1991 | Loiterman et al. | ............ | 604/175 |
| 5,578,006 A * | 11/1996 | Schon | ........................ | 604/93.01 |
| 5,713,858 A | 2/1998 | Heruth et al. | | |
| 5,723,005 A * | 3/1998 | Herrick | ........................... | 623/4.1 |
| 5,843,150 A | 12/1998 | Dreessen et al. | | |
| 6,419,281 B1 * | 7/2002 | Salomon-Bahls et al. | .... | 285/307 |
| 6,923,799 B1 | 8/2005 | Asfora | | |
| 2004/0092910 A1 * | 5/2004 | Harper et al. | ................. | 604/540 |
| 2005/0131352 A1 * | 6/2005 | Conlon et al. | ................ | 604/175 |
| 2006/0253104 A1 * | 11/2006 | Pandey et al. | ................. | 604/540 |
| 2007/0083146 A1 * | 4/2007 | Murray | ............................. | 604/8 |
| 2007/0088280 A1 * | 4/2007 | Gomez | ............................. | 604/174 |
| 2007/0239107 A1 * | 10/2007 | Lundberg et al. | .......... | 604/96.01 |

* cited by examiner

*Primary Examiner* — Leslie Deak
*Assistant Examiner* — Xin Xie
(74) *Attorney, Agent, or Firm* — Andrew S. Langsam; Pryor Cashman LLP

(57) ABSTRACT

A subcutaneous drain, preferably for implantation into the skull of a patient comprises a basically hollow cap and a stem with an inside, central passageway passing from top of the cap through the stem. A lumen is provided through at least a portion of the inside, central passageway with the lumen preferably exiting the cap through a side slit in the cap and stem. The lumen is provided with a supporting ledge to reduce kinkage and promote an unimpeded fluid path. The side slit is resilient to allow for the selective removal of the lumen. The cap and stem are, as mentioned, substantially hollow and defines a chamber in communication with the subdural space, so that with the device in place, a physician can use a hypodermic needle to gain access to fluid in the subdural space by piercing the needle tip of the hypodermic syringe or needle through the thin wall of the cap of the device. A circumferential flange is provided to facilitate location of the device. Also, the stem is slightly inwardly tapered.

17 Claims, 7 Drawing Sheets

SUBCUTANEOUS DRAIN FOR A BODY CAVITY

BACKGROUND OF THE INVENTION

The present invention relates to the field of medical devices. This device is intended to be selectively implanted beneath the skin of the patient and provides a mechanism which will allow for drainage of a body cavity or, alternatively, the introduction of medication into a body cavity. For example, a patient having fluid in their chest that keeps recurring can have the device of the present invention implanted under the skin, over the ribs and the open end of the stem can be located in the pleural cavity. The same device can be used in the abdomen sot that if fluid collects, for example, in the peritoneal cavity, the cap of the device can be beneath the skin and the open end of the stem below the peritoneum.

Preferably, however, the device can be implanted into a human patient below the skin of the head but above the hard skull for draining the subdural cavity and/or providing medication thereto. For ease of illustration and reading, and in that the present invention has its preferred embodiment for use in connection with the subdural cavity, the present invention will be described for that purpose, it being understood by those reading the same that the invention is not so limited but, rather, will extend in scope to other human drainage usages and/or provision of medication to a human, beneath the skin and into a cavity. The scope of the invention is intended to extend to the fullest extent of the scope of the appended claims as worded and as interpreted by the Courts.

In the preferred embodiment, then, a subdural drain is provided which has one portion above the skull and below the skin while the other portion of the device extends through the skull and into the subdural space. That space is generally considered to be the area or volume which is between the inside of the hard skull and the brain. The present invention is a subdural drain which is intended to allow for selective removal of fluid from the subdural space or the introduction therein of medication, all under a physician's care and guidance. The device can be left in situ for extended periods of time and thus allows the physician to properly treat his or her patient by either allowing for selective drainage (either by use of a hypodermic syringe sucking out fluid, the syringe passing through the cap of the device or by a drainage bag being secured to the tube extending through the device and into the subdural space) or for selective providing of medication (again, by use of a loaded-with-medication syringe directed into either the tube and/or the cap of the device which allows the medication to flow into the subdural space). If and when deemed necessary, the device can be removed from the skull and discarded and then the skull plugged and the skin thereover sutured or otherwise secured back.

The present invention is a basic mushroom-shaped, preferably silastic drain for placement under the skin with the cap of the mushroom shape beneath the skin of the skull and brain but above the skull and the stem of the mushroom shape passing through the skull and into the subdural space for selectively draining of fluid or providing medication from and to the subdural space. Preferably, the cap and stem of the device define a substantially hollow device with an opening directed towards the bottom of the stem. In the preferred embodiment, a L-shaped lumen passes through the center of the stem and extends into the subdural space and out of the top of the cap of the device and through the patient's skin. The L-shaped lumen (a tube with a bore) allows the device to act as a fluid drain when it is connected to a drainage bag and the bag is located below the height of the subdural space. Gravity will thus allow for drainage. If the bag is filled with medication, however, and located above the height of the subdural space, then it will flow into the subdural space at least until the pressure on the inside (within the subdural space) equalizes with the pressure and weight of the fluid in the drainage bag. Alternatively, the subdural drain can be used with a hypodermic syringe aspirating fluid from the subdural space. In this procedure, the physician would poke the syringe either into the lumen or directly into the cap of the subdural drain. The syringe would either aspirate and withdraw excess fluid (or fluid withdrawn for analysis) or if the syringe were preloaded with medication the syringe would selectively inject the subdural space (through either the lumen or the hollowed toward the bottom of cap and stem) with medication.

DESCRIPTION OF THE PRIOR ART

Subdural drains have been provided by others. Indeed, several US Patents have issued for such basic devices. However, it appears that the manner of construction and operation of the prior art subdural drain devices suffer from one or more disadvantages. It is, therefore, an object of the present invention to overcome one or more of the disadvantages of the prior art subdural devices.

U.S. Pat. No. 3,310,051 ("the '051 Patent") to Schulte issued in 1967. It shows a surgical reservoir for implanting beneath the skin and, according to the description is meant for installation in a burr hole in the bone of the skull, intended to be held beneath the skin of the scalp. The entire structure is preferably made of silicon rubber. A tube 21 with a central passage 22 and a closed end 23 is provided. A perforation 24 is maintained through the wall of the tube (See FIG. 1) to provide fluid communication between the tubular passage and the outside of the tube 21. The cap of the mushroom shape is referred to in the US Patent as the capsule and is provided with a boss (cylindrical extension) 29 which fits within the burr hole 14. The capsule, outside of the boss rests on the top surface of the skull. The central passage is comprised of a few elements and the fluid conduit is provided for draining fluid from the subdural space through the stem of the capsule and then out through a side opening, when a suctioning hypodermic is provided and aspiration accomplished. The description also indicates that the device is intended to remain in place for "sensible periods of time." (See Column 3, line 25). No mechanism is provided for selective drainage by use of a drainage bag and no means is suggested for providing a tube which extends out through the device, through the skin (the lumen of the present invention) for allowing drainage by gravity and/or provision of medication. Rather, the '051 device seems to allow suck fluid out and introduce medication into the subdural space by the use of a hypodermic syringe.

A key point of the '051 device is that there is no provided no permanent outward passage from the central tube but, rather, the physician must use a syringe to drain the fluid.

The present invention however provides a lumen for allowing for drainage by use of a drainage bag and does not require (although it is an option) that a physician use a hypodermic syringe for drainage. Also, according to the '051 Patent, the silicon-rubber-like composition is meant to allow the cap to flex in both directions i.e., to expand outwardly away from the skull or to compress toward the skull and the notches on the inside of the cap (See FIG. 4) prevent the total, long term collapse of the device.

U.S. Pat. No. 5,713,858 to Heruth et al. was originally assigned to Medtronic, Inc. It relates to a permanently implantable guiding catheter intended for cranial implantation. A burr hole 26 is formed in the skull 14. The catheter 16 is inserted therethrough until its distal end 15 is located beneath the skin 12. The access port 17 is then attached to the proximal end of the catheter 16. Then the skin 12 is closed on top of port 17. A needle 22 is selectively poked into the cap and the catheter installed whereupon the needle removed. A splitable needle is discussed as being useful for this purpose. The cap 20 self-seals around the catheter or in the absence of a catheter (See FIGS. 5 and 6) and drugs can be infused or liquid sucked out. Removal of the catheter seals the passageway yet the device can be reused by reintroducing a needle through the dome 20 and through the spring loaded (outwardly resilient) latch or sealing mechanism 26.

U.S. Pat. No. 5,843,150 to Dreessen et al. is a system for providing electrical and/or fluid treatment within a patient's brain. The invention disclosed therein, too, is desirably mushroom shaped and made of silicon rubber. Here, however, the mushroom shape is secured with the cap above the skull by a clip-like device which surrounds the stem above the skull but beneath the cap. Viewing the Figures, one sees the change of shape of the central bore as it extends from central bore to the outside surface of the cap member. A burr is first formed in the skull. Then the plug like device is placed with the stem in the burr. This is clearly shown in FIG. 7A. Then, the clip element 40 (See FIGS. 2A and 2B) is laterally placed and snapped around the plug device (See FIG. 7B). Then, the cap, element 50 is placed (See FIG. 8) over the plug and securing clip. A laterally extending lead 60 is provided and seemingly provides fluid communication between the inside channel of the plug (and the subdural space therebelow) and the outside so that fluid can be removed, as desired, or introduced, too.

U.S. Pat. No. 6,92,799 to Asfora also relates to a subdural evacuating port system. It, too, is placed into a drilled burr in the skull of a patient. FIGS. 1, 5 and 7 clearly show the device. The wings 52 and 54 secure the device above the skull while the plug element with central channel or passageway are directed into the subdural space. Suction can be provided to the first end 30 via a tube 22 or, alternatively, medication can be introduced into the subdural space through the same fluid passageway.

U.S. Pat. No. 4,677,985 shows an apparatus and method for determining intracranial pressure and local cerebral blood flow. Turning to FIG. 6 thereof and the related description in Column 7, line 26+, a burr hole 200 is provided into skull 201. A pressure probe 210 (shaped like a mushroom) extends into the hole 200 and is held in place by suitable adhesive. The probe 210 is a pressure transducer for sensing and measuring (and providing a signal of the same) the pressure of the fluid within the subdural space. A biomedical transducer for this purpose is specifically identified. Also, flow is sensed at flow probe 215.

Based on the above, the general concept of a subdural drain, located beneath the skin but passing through a bore drilled into the skull is old. However, the present invention represents significant improvements in providing versatility in the application and use of the device by providing select features and construction which are neither anticipated nor suggested by the known prior art, either when that art is individually considered or even if combined with one another. A mushroom shape wherein the cap is above the skull and the stem passes through the skull and into the subdural space is seemingly shown in the applicable art. Furthermore, providing a fluid pathway through the stem, into the cap and to the subdural space for evacuating fluid seems old, too. However, as will be seen, the present invention provides additional versatility and features as a consequence of its construction and should be quite helpful to medical professionals. Providing the option to the physician to aspirate or introduce medication through the cap of the mushroom shape of the subdural drain and, alternatively, by use of a fluid path provided by a lumen so that gravity will either draw fluid or introduce the same out of and into the subdural space is valuable to the medical professional. Also, the present invention provides a support for the lumen, as it exits the mushroom cap. That support ensures constant fluid communication into and out of the subdural space and against kinkage or blockage of and within the lumen. A side slit or opening in the mushroom portion of the device allows the physician to easily and quickly place a lumen into the device and remove the same. This is facilitated by the resiliency of the device and the side slit. In addition a central-located opening is provided which will give the physician direct access (by hypodermic syringe) to the lumen or into the subdural space. These and other features provide a superior new subdural drain, a significant advance(s) over the prior art devices.

SUMMARY OF THE INVENTION

The present invention represents a new subdural drain with versatility and features previously not provided by the prior art. Basically, the device is a substantially hollow mushroom shape, with cap and central, downwardly extending stem. The stem will, after a suitable bore is drilled into the patient's skull (beneath the skin, of course) extend down and toward (and in, if dimensioned for that purpose) the subdural space of the patient, i.e., the space of the head which exists between the brain B and the skull Sk (see FIG. 7). Fluid can accumulate in that space and it is often desirable to remove the same for advancing the medical condition of the patient and, yet, it can become desirable for fluid to be introduced into that same space to treat the patient. The device has a central bore extending from top of the cap through the stem. This provides a first fluid communication path. The lower edge of the cap is provided with a circumferential flange to allow the device to be selectively sutured to the skull for short or long term placement. Extending laterally from top of the cap, down the side wall of the cap and to the stem is a side split of slit. This slit allows for the physician to easily place a selected lumen into the device, if desired. The resiliency of the preferably silastic material allows the opening of the slit so that placement of the lumen is easily accomplished and, yet, after the lumen is placed, the resiliency of the device "snaps" back to its original shape and thus captures and holds the lumen in place. The same side slit and resiliencey allows for the removal of the lumen by the physician, if and when desired. The physician can simply grab the free end of the lumen, extending beyond the side surface of the cap of the device and by pulling thereon the lumen will be pulled free of the device.

A supporting ledge is provided to the device. It extends laterally and is basically aligned with the side slit. The supporting ledge provides a support surface for the lumen and ensures that minimal, if any, kinkage or blockage of the lumen is present.

In operation, a bore is first drilled into the patient's skull, beneath the skin surface. Then, the stem of the device is placed into the bore and the device can, if medically desirable, be sutured by sutures or staples passing through the outside flange and into the skull. With the device in place, the introduction of fluid or medication into the subdural space can result in medically beneficial procedures. Alternatively, the removal of fluid in the subdural space can take place. The fluid (whether into or out of the subdural space) can either be introduced or withdrawn through the central opening of the device, preferably by syringe or through the cap itself, by syringe. If a lumen is placed into the device, through the side slit and supported by the supporting ledge, before installation of the device into the patient's head, then that lumen can serve as a fluid pathway for the introduction of fluid or for its gravitational removal, into a drainage bag. If desired, as determined by the physician, the lumen can be removed, after it has served its function (or not even inserted into the device at the beginning if the physician knows beforehand of it not being necessary) by pulling on the same. The resiliency of the device will allow for the removal of the lumen while the device is still held in place by the stitches, adhesive or merely by the resiliency of the product and the relative dimensioning of the bore, the stem, etc.

After the medical necessity for the device is finished, the physician can remove the device.

DETAILED DESCRIPTION OF THE DRAWINGS AND THE PREFERRED EMBODIMENTS OF THE INVENTION

Figure 1:
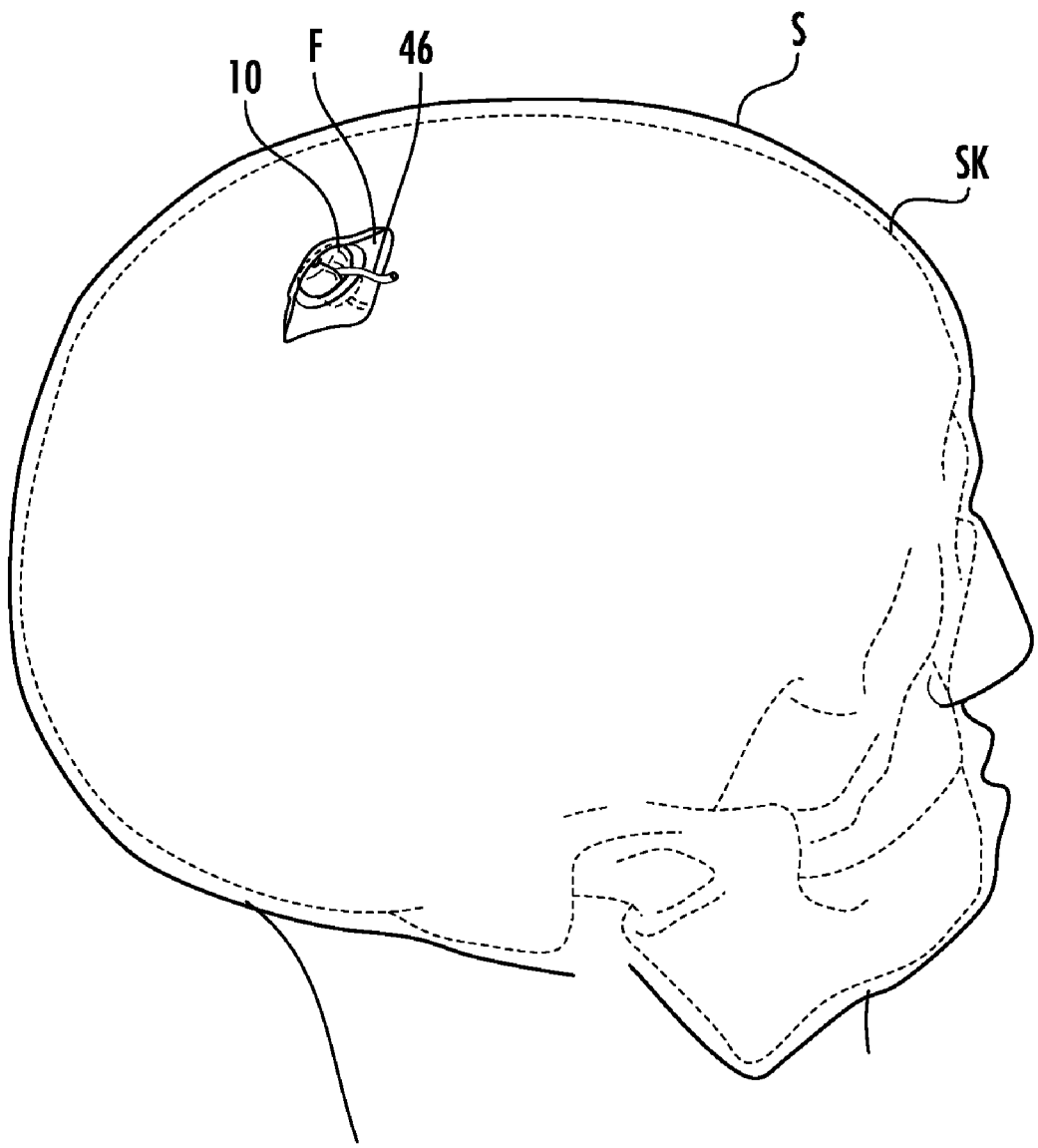
FIG. 1 is a rear perspective view of a human skull, showing a flap of skin and the device located beneath the flap yet with the lumen of the device extending above the skin and the skull on the outside and the distal end of the lumen extending through the device and into the subdural space of the patient.
Figure 2:
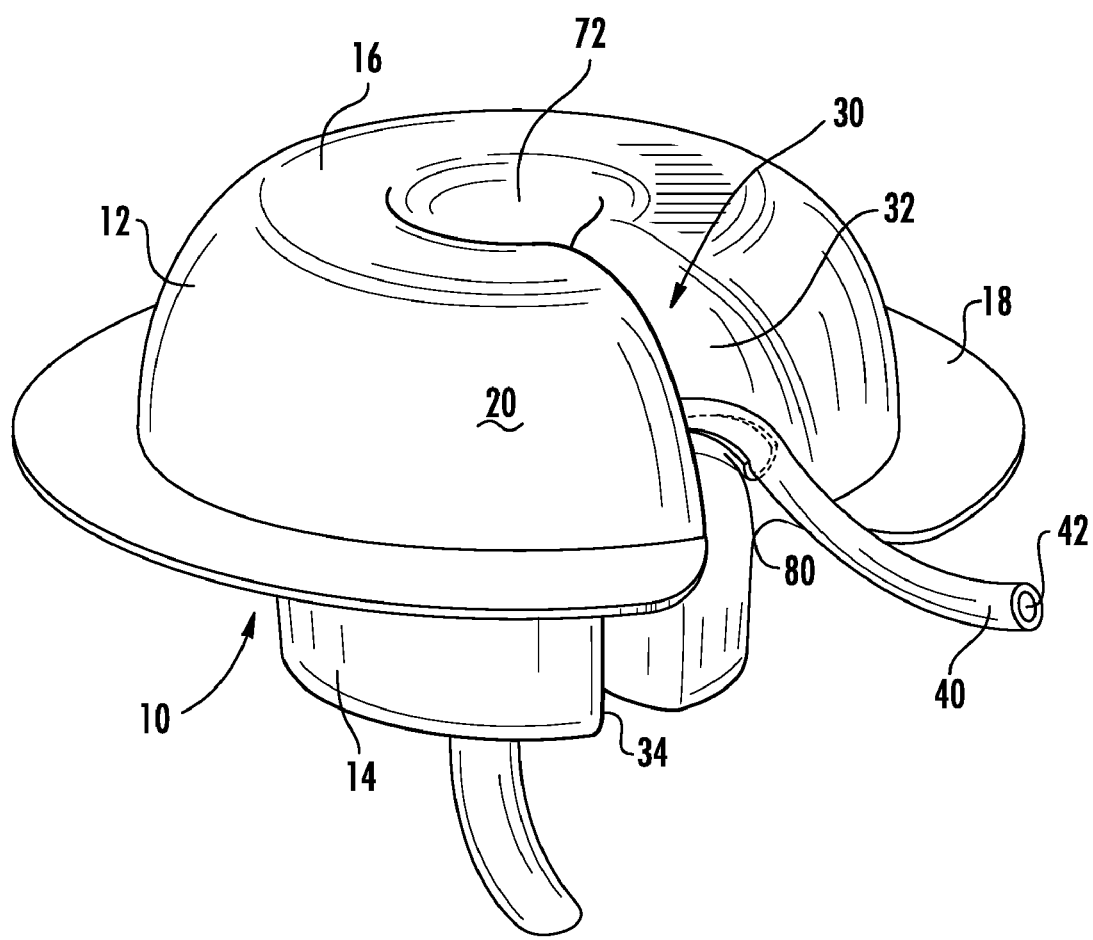
FIG. 2 is an enlarged perspective view of the device, the side slit, supporting ledge and lumen.

Referring first to FIG. 2, the invention basically comprises a preferably silastic or other bio-compatible material, preferably with resiliency, which is in a basic mushroom shape. The subdural drain 10 comprises a top or cap section 12 and a stem 14. The cap 12 has preferably a smooth outside wall 20, and is shaped substantially semi-spherically although the top section 16 can be flattened. At the base of the cap 12, extending outwardly from the smooth outside wall 20, is a thin, outwardly extending flange 18. This flange 18 facilitates the sccurement, as desired, of the subdural drain 10 to the skull, beneath the patient's skin, by providing adequate surface for suturing the same to the skull. Of course, other means (or none at all) can be used to secure the subdural drain into position and to the outside surface of the skull.

Figure 5:
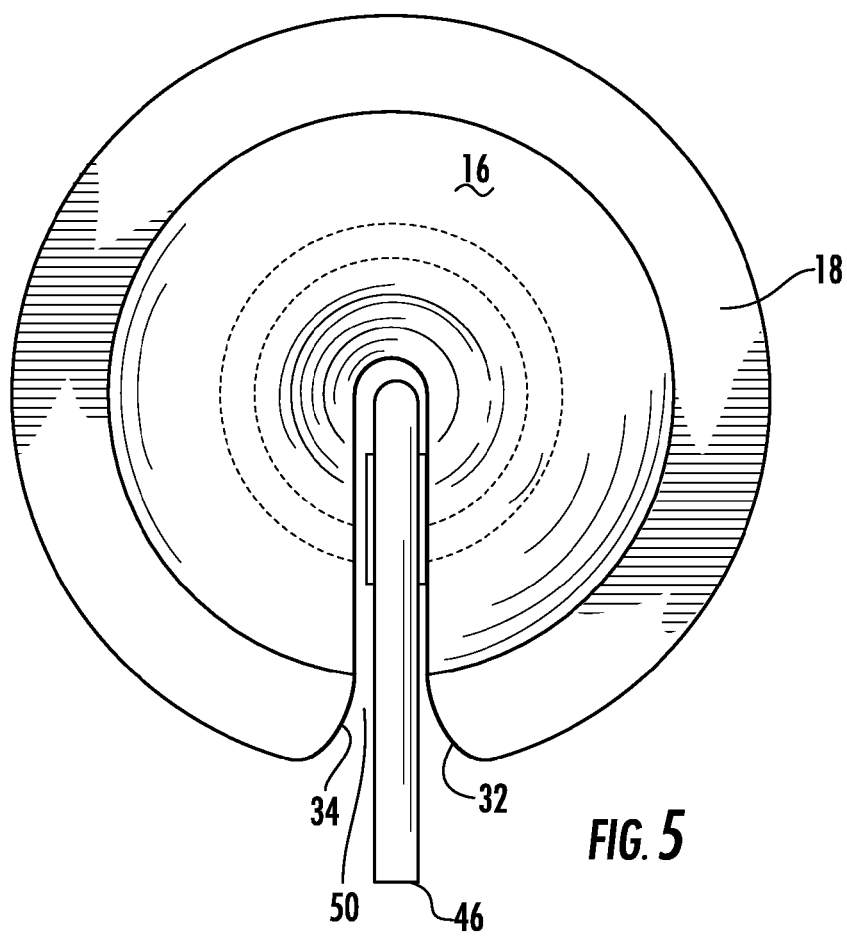
FIG. 5 is a top plan view of the device and shows the lumen extending laterally as it leaves the skull and yet also shows the central length of lumen being supported by the supporting ledge, at the side slit.

A side slit 30 extends from the flattened top section 16 to the side wall 32 of the stem 14. The side slit 30 provides an opening which passes through the wall of the cap section 12, through the flange 18 and through the stem 14. The side slit 30, as will be explained, allows for a lumen or tube 40 with a central bore 42 to be placed into the device, before it is implanted into a patient, and, in addition, allows the device to be easily removed from the device, when the lumen is no longer desired or needed. The material of the device and especially at the side slit 30 is desirably resilient so that the sides of the slit can be physically pried open to allow for placement or removeal of the lumen 40 and then a release of the side walls 32 and 34 of the side slit 30 causes the side slit 30 to resume its original position with the lumen 40 contained therein or removed therefrom. The side slit thus flexes outwardly by pushing outwardly on walls 32 and 34 and, then, when those walls are released, the side slit is back to its original opening dimension, a consequence of its resiliency. The side slit 30 can be provided with curved outside edges, at the split 50 (See FIG. 5) of the flange 18 to facilitate the physician's outward movement and release of the flange to open up and allow the closure of the side slit 40.

Figure 3:
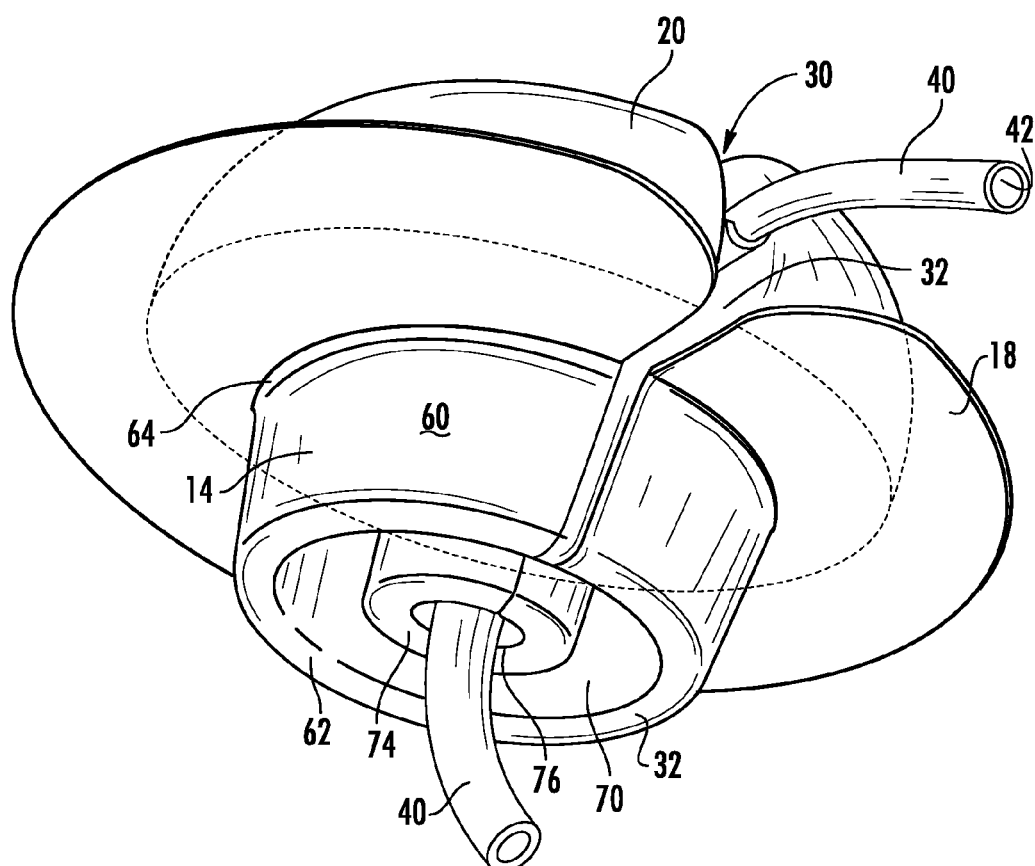
FIG. 3 is a bottom perspective view of the device, similar to that shown in FIG. 2 and more clearly shows the distal end of the lumen and the manner by which extends out of the central opening of the stem, as it will become in fluid communication with the subdural space of the patient.

Looking at the bottom of the device, specifically at stem 14 (See FIG. 3, it is comprised of a primary wall 60 which extends downwardly and yet is inwardly recessed from the underside of the flange 18. The primary wall 60 is basically cylindrical, yet slightly tapered inwardly and is again preferably formed of silastic material. The inward taper of primary wall 60 allows the device to be installed and implanted into bores through the skull of varying dimensional diameters. The taper allows the device to be installed into those bores of diameter which is slightly larger than the minimum outside diameter at the bottom edge 62 of the primary wall 60 and into those bores of diameter slightly more than the maximum outside diameter at the top edge 64 of the primary wall (at the location where the primary wall 60 merges into the underside of the flange 18 (See FIG. 3). In addition, the taper allows for use of the device and implantation into bores drilled into skulls where the diameter of the bore is between the minimum and the maximum in that the stem 14 will slide downwardly into the bore and snugly be held there by the frictional engagement between the outside of the stem 14 (primary wall 60) and the inside edge of the bore drilled in the patient's skull.

Figure 4:
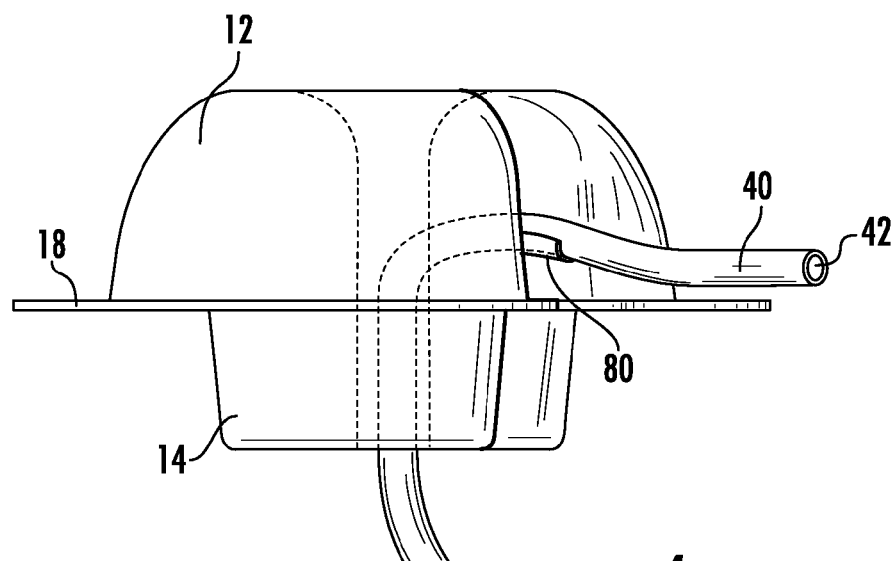
FIG. 4 is a side elevational view of the device of the invention and shows the pathway of the lumen as it passes from subdural space at the distal end of the lumen, throught the central opening or passageway, then turns laterally and is supported by the supporting ledge (a partial tube shape) and then above the flange of the device.
Figure 6:
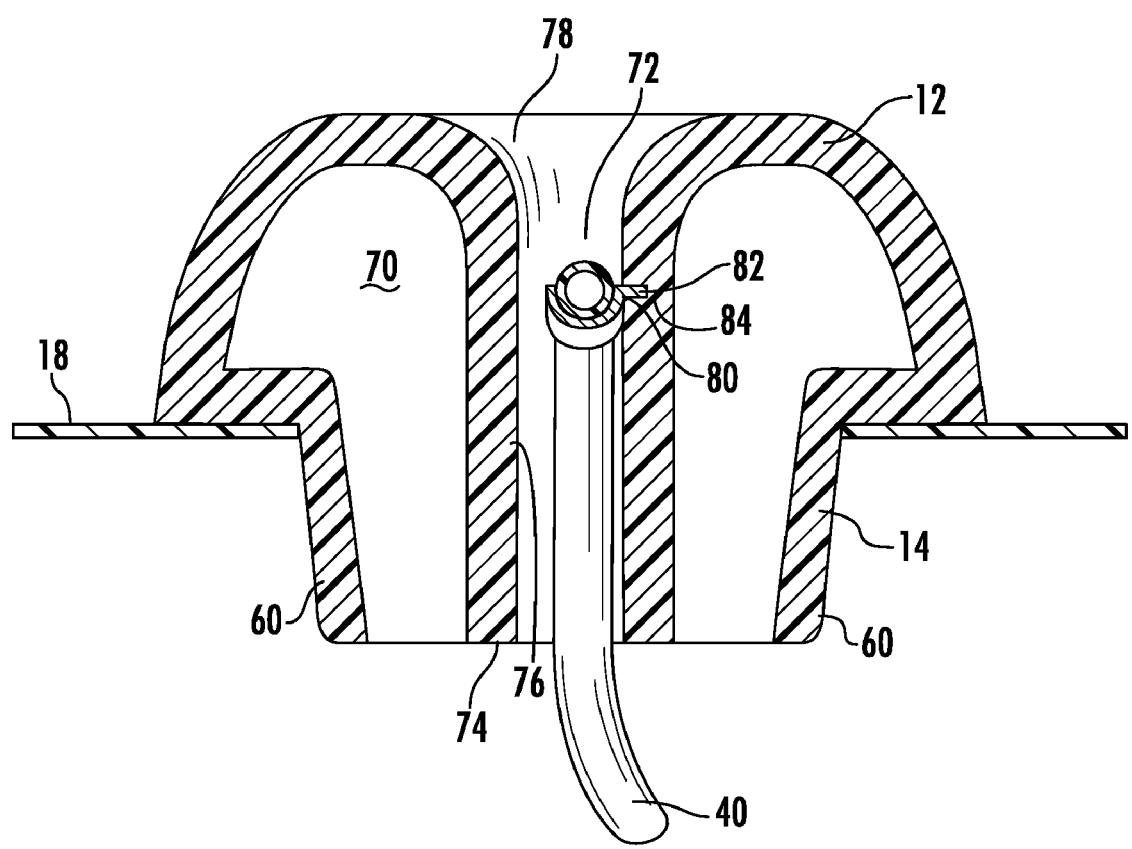
FIG. 6 is a side cross sectional view of the device, showing the circumferential flange (for securing the device to the skull), the substantially hollow mushroom-shaped cap and its stem and the lumen, supported in the central passageway for its distal length and then on the supporting ledge, as it extends laterally out of the device, through the side slit.

Directing the reader's attention to FIG. 6, one realizes that the subdural drain, comprising cap 12 and stem 14 is substantially hollow. A chamber 70 is defined by the cap 12 and between the outside wall or primary wall 16 of the stem 14, the flange 18 and the inside, central passageway 72. The inside, central passageway 72 is defined by a bottom edge 74, a smooth walled inside wall 76 and a top opening 78. The inside, central passageway provides a pathway from the top of the cap 12 of the subdural drain 10 down the center of the device and into the subdural space of the patient. The top opening 78 is preferably outwardly flared and provided with a smooth wall, too. Stated another way, as can be seen in FIGS. 2, 4, and 6, the inside, central passageway is outwardly flared toward the top of the cap. The inside diameter of the inside, central passageway 72 is greater than the outside diameter of the lumen 40 and the lumen 40 thus is housed and passes from outside into the subdural space by the lumen 40 being placed in the lower portion, i.e., beneath the top opening 78, of the inside, central passageway 72.

Figure 7:
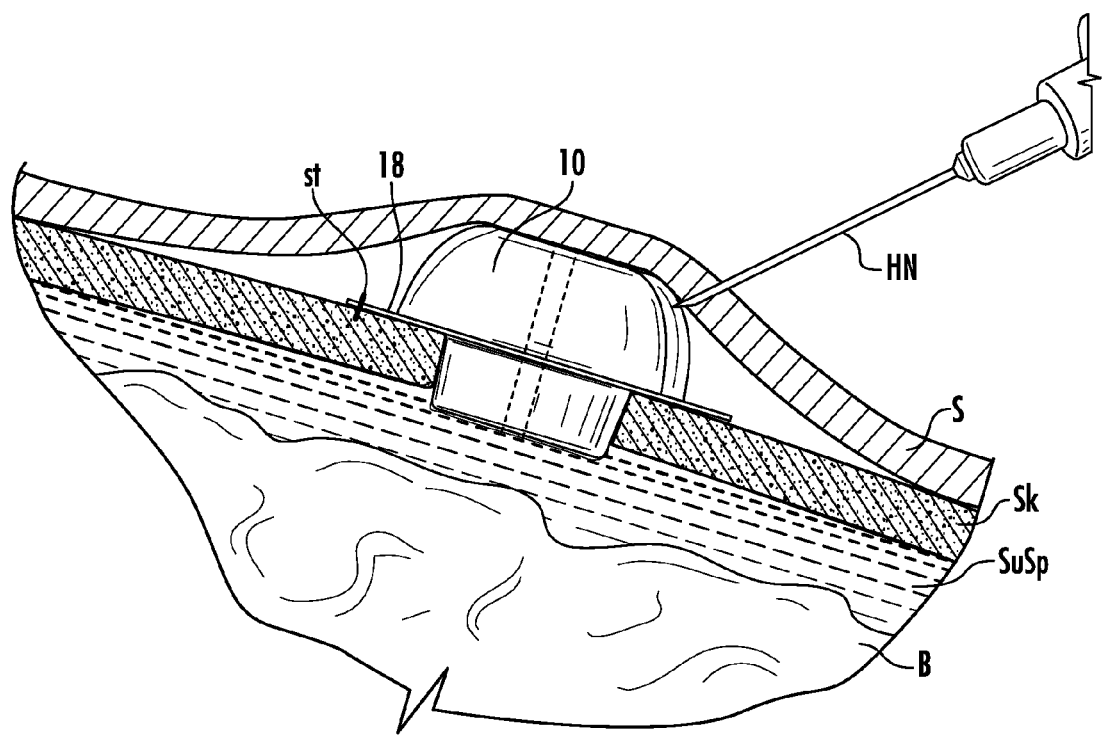
FIG. 7 is a cross-sectional view of the device as it is installed or implanted into a patient's skull and shows the device beneath the skin, sutured in place, with the stem passing through a bore of the skull and the stem extending into the subdural space—this view shows the removed (or never installed) lumen and also shows a syringe passing through the skin and into and through the cap of the device for removal of fluid and/or introduction of medication therethrough.

The chamber 70, as can be seen in FIGS. 3 and 6 is open towards the bottom and thus fluid can be passed into and/or drawn up into chamber 70 and removed therefrom by the selective insertion of a hypodermic needle HN (See FIG. 7) when the same pierces the skin S, the smooth outside wall 20 of the cap 12 and into the chamber 70.

A supporting ledge 80 (preferably in the form of a half-pipe) is secured to the inside wall of the inside, central passageway 72, the supporting ledge 80 has a short length, flat flange 82 which is held in a slot 84 of the inside, central passageway 72. The supporting ledge 80 is preferably held there by adhesive, by frictional engagement between the silastic material and the supporting ledge 80 or by other means. The supporting ledge 80 is preferably located about ⅔ of the way up the inside, central passageway 72 from the bottom edge 74. Preferably the curvature or shape of the supporting ledge 80 corresponds to the outside wall of the lumen 40 so that the lumen, when placed into the side slit 30, is upwardly supported by the supporting ledge 80.

Figure 8:
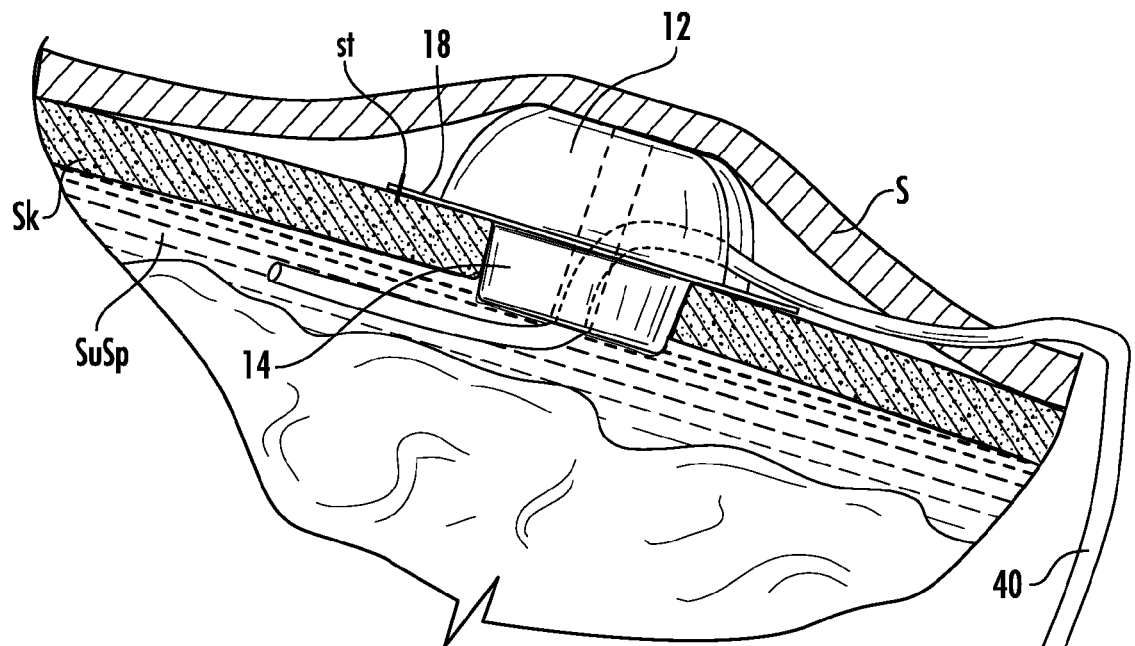
FIG. 8 is a view similar to that of FIG. 7 in that it is a cross-sectional view of the device as it is installed or implanted into a patient's skull and shows the device beneath the skin, sutured in place, with the stem passing through a bore of the skull and the stem extending into the subdural space—this view shows the lumen in place for the drainage of fluid out of the subdural space, through the lumen, out of the skull and through and out of the skin and into a gravity-based drainage bag.
Figure 8:
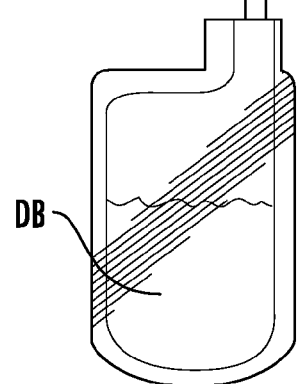

As can be seen from the drawings, the lumen 40 passes and thus provides a fluid passageway as follows: extending into the subdural space SuSp (See FIG. 7); upwardly into the bottom of the inside, central passageway 76, then extending laterally and outwardly from the inside slit 30, supported on the supporting ledge 80, and then laterally out of the device, possibly laying upon the flange 18, and through the skin S (See FIG. 8). If used with a drainage bag DB, gravity will allow for removal of fluid from the subdural space SuSp and into the drainage bag DB. If the drainage bag DB is held above the level of the subdural space SuSp, then fluid with medication within the bag will drain by gravity into the subdural space SuSp (and, yet, of course, this can be easily regulated by the use of a clamp on the lumen 40 to close off or decrease the inside diameter of the opening 40 of the lumen).

In operation and use, the subdural drain is implanted by a physician using ordinary and standard medical procedures. Prior to implantation, the physician will either select the subdural drain with a lumen 40 already in place or he/she will install the lumen into place. This, as mentioned, is an easy procedure as a consequence of the resiliency of the walls of the inside, central passageway, the opening of the flange and the side slit and the relatively smaller diameter of the lumen, in comparision to the diameter defined by the inside, central passageway 76. In some cases the physician will select a subdural drain without a lumen, in other situations, the physician will implant the subdural drain with the lumen in place, even though later he/she will remove the lumen from the device.

When a subdural drain or port is required, the physician will first cut a flap F into the patient's skin S, slightly greater than the outside dimension of the subdural drain 10. Beneath the flap F, the physician will then drill a small bore through the patient's skull Sk, providing a pathway from the top of the patient's head through the skull Sk and into the subdural space SuSp. Then, the stem 14 of the subdural drain 10 is placed into the bore formed in the skull Sk and lightly pushed downwardly until the outside of the stem 14 fits snugly into the bore and the subdural drain 10 is held in place by friction. In the preferred embodiment the drill used for creating the bore is sized so that the stem fits fully down into the bore with the flange 18 lying just upon the skull Sk. The flap F allows the subdural drain 10 to be placed beneath the skin (beneath the flap F).

Once the stem and flange are in place, with the stem through the bore of the skull Sk and the flange 18 resting upon the outside of the skull Sk, the physician can secure the same in place by using one or more sutures, staples, or other adhesive/securing means. Of course, no such supplementary securement may be needed in that it is a preferred embodiment of the invention that the frictional engagement of the outside wall 60 and the edge of the bore hold the device in place and do so in an airtight and fluid-tight manner. The use of resilient material, preferably silastic compound for the outside wall (if not the entire subdural drain) of the stem promotes the holding of the device in place in the fluid and air-tight manner.

With the device in place, the distal end of the lumen 40 (if a lumen is originally provided to the patient) is located within the subdural space SuSp or if no lumen was originally used with the subdural drain, the lower or bottom edge 74 of the inside, central passageway 72 is within the subdural space SuSp. Also, the opening of the chamber 70 of the device is directed toward and into the subdural space SuSp. This allows the physician to drain or medicate the patient by a variety of pathways. For example, the fluid pathway defined by the lumen 40 allows fluid to be removed (as by drainage bag DB) by starting suction and then lowering the drainage bag DB below the level of the subdural space SuSp. Alternatively, if the drainage bag is filled with medication, then the same can be lifted above the subdural space SuSp and gravity flow will cause medication to flow into the subdural space. Equilibrium of the pressure within and without the subdural space will cause the flow of liquid to stop.

In addition, the physician may, at his/her discretion, decide to remove the lumen from the device. The device will still, however, remain implanted. The physician can grab, with forceps or fingers, the free outside end of the lumen and pull the same. The side slit 30 facilitates the easy removal of the lumen from the subdural drain. The lumen will easily pass out of the device by the resiliency of the side slit, the opening in the flange and the presence of the side slit. Thus, the entire lumen 40 can be selectively removed. After removal, however, the resiliency of the side slit is such that it closes itself back together and the inside, central passageway is thus provided as another pathway for the removal of fluid and the introduction of fluid, as required by the patient, as determined by the physician. The inside, central passageway 72 can be accessed by the physician via a hypodermic needle HN, if desired. This will allow removal of fluid and introduction of fluid into the subdural space SuSp via the pathway defined by the inside, central passageway.

Alternatively, with or without the lumen removed, the physician can remove fluid or introduce the same (as a medication) by accessing the chamber 70. This is done by the physician using a hypodermic needle HN which pierces the cap 12 of the subdural drain with the tip of the hypodermic needle passing into the chamber 70. Since the chamber 70 is open toward the bottom of the device, aspirating the hypodermic needle HN will suck up fluid which has traveled up into the chamber 70. Medication or fluid can also be introduced into the chamber (and thus into the subdural space SuSp) by the use of the same or a different hypodermic needle FIN whose needle tip pierces the skin S of the patient and then into and through the thin wall of the cap 12 of the subdural drain (See FIG. 7).

If the device is to be removed from the patient, the physician can remove the same by cutting the sutures or staples St or by otherwise disabling the securing mechanism. Then the device can be removed from the skull Sk and the flap F resewn to the skin S of the patient.

While the present invention has been fully described by the present specification when read and viewed in association with the described drawings, the invention is not to be limited to the shown invention but, rather, the scope of protection to which the inventor is entitled is defined by the claims, as set forth herein and as interpreted by the Courts. The inventor desires and claims the full scope of his invention, as defined herein and as allowed by the manner by which the present invention represents a patentable advance over the prior art, either when the art is individually considered or even if combined with one another.

I claim:

1. A subcutaneous drain comprising:
   a basically hollow mushroom shape defined by a cap, having a top, and a stem having a bottom;
   b) an inside, central passageway passing through said cap and said stem and defining a fluid pathway from said top of said subdural drain to said bottom, said subdural drain having an outwardly flared surface extending upwardly from said inside, central passageway towards said top of said cap;
   c) a lumen passing at least partially through said inside, central passageway; and
   a resilient side slit passing through said cap and said stem, said side slit extending completely from said top of said cap to said bottom of said stem and allowing for said lumen to be selectively removed from said inside, central passageway by passing the same through said side slit.

2. A subcutaneous drain as claimed in claim 1 wherein said stem is slightly inwardly tapered.

3. A subcutaneous drain as claimed in claim 1 wherein a laterally extending flange is provided at a location of said drain at about the bottom of said cap and the top of said stem.

4. A subcutaneous drain as claimed in claim 1 wherein said side slit is provided with a supporting ledge for said lumen.

5. A subcutaneous drain as claimed in claim 1 wherein said inside, central passageway is greater in inside diameter than the outside of the diameter of said lumen.

6. A subcutaneous drain as claimed in claim 1 wherein the outside of said inside, central passageway and the inside of said stem defines a bottom opening for said device.

7. A subcutaneous drain as claimed in claim 1 wherein said stem and said cap define a hollow chamber, opened toward the bottom of said subdural drain.

8. A subcutaneous drain as claimed in claim 1 wherein said cap is smooth walled and roughly semi-spherical and said stem is smooth-walled and basically cylindrical.

9. A subcutaneous drain as claimed in claim 8 wherein said stem is inwardly tapered from its top to the bottom of said stem.

10. A subcutaneous drain as claimed in claim 3 wherein said side slit also extends through said flange.

11. A subcutaneous drain as claimed in claim 10 wherein said flange is provided with opposed ends adjacent to and defining therebetween said side slit and said opposed ends are curved to facilitate the spreading of said side slit.

12. A subcutaneous drain as claimed in claim 4 wherein said supporting ledge is secured to said inside, central passageway.

13. A subcutaneous drain as claimed in claim 1 in combination with a drainage bag.

14. A subcutaneous drain as claimed in claim 1 made substantially entirely from resilient and bio-compatible material.

15. A subcutaneous drain as claimed in claim 1 wherein said cap is thin-walled and resilient to allow for the passage of a tip of a hypodermic needle and upon removal of the same to close up said cap so that the same is substantially air and fluid tight.

16. A subcutaneous drain as claimed in claim 3 wherein said flange is thin walled to allow for the use of sutures for securing said device to the skull of a patient.

17. A subcutaneous drain as claimed in claim 1 wherein said inner, central passageway provides a fluid pathway with said lumen therein and a fluid pathway even if said lumen is removed.

* * * * *